United States Patent [19]

Shimasaki et al.

[11] Patent Number: 4,731,488
[45] Date of Patent: Mar. 15, 1988

[54] VAPOR-PHASE HYDROGEN TRANSFER REACTION OF CARBONYL COMPOUND WITH ALCOHOL

[75] Inventors: Yuuji Shimasaki, Suita; Youichi Hino, Sakai; Michio Ueshima, Takarazuka, all of Japan

[73] Assignee: Nippon Shokubai Kagaku Kogyo Co., Ltd., Osaka, Japan

[21] Appl. No.: 873,447

[22] Filed: Jun. 6, 1986

Related U.S. Application Data

[62] Division of Ser. No. 802,183, Nov. 25, 1985, abandoned.

[30] Foreign Application Priority Data

Nov. 27, 1984 [JP] Japan ................... 59-248650
Apr. 8, 1985 [JP] Japan ................... 60-72698

[51] Int. Cl.⁴ .............. C07C 29/136; C07C 29/14; C07C 33/03; C07C 33/22
[52] U.S. Cl. ................... 568/648; 502/202; 502/242; 502/303; 502/341; 568/813; 568/814; 568/825; 568/881
[58] Field of Search ............... 568/814, 880, 881, 846, 568/825, 813

[56] References Cited

U.S. PATENT DOCUMENTS

| 1,844,963 | 2/1932 | Larson | 502/243 X |
|---|---|---|---|
| 1,866,246 | 7/1932 | Beekley | 502/242 X |
| 2,369,074 | 2/1945 | Pitzer | 502/251 X |
| 2,633,475 | 3/1953 | Mattern | 502/340 X |
| 2,767,221 | 10/1956 | Ballard et al. | 502/38 X |
| 2,889,266 | 6/1959 | Baker et al. | 502/202 X |
| 2,932,673 | 4/1960 | Melik et al. | 502/340 X |
| 3,551,497 | 12/1970 | Wymore | 568/814 X |
| 3,901,947 | 8/1975 | Enomoto et al. | 502/304 X |
| 3,962,134 | 6/1976 | Cobb | 502/202 |
| 4,072,727 | 2/1978 | Vanderspurt | 502/243 X |
| 4,096,193 | 6/1978 | Vanderspurt | 502/340 X |
| 4,255,283 | 3/1981 | Bartek et al. | 502/202 |
| 4,407,732 | 10/1983 | Kehl | 502/208 |
| 4,418,005 | 11/1983 | Dodd et al. | 502/340 X |
| 4,471,070 | 9/1984 | Siefert et al. | 502/341 X |

FOREIGN PATENT DOCUMENTS

| 5549322 | 10/1978 | Japan | 502/340 |
|---|---|---|---|
| 727209 | 8/1977 | U.S.S.R. | 502/340 |

OTHER PUBLICATIONS

Selective Reduction of Unsaturated Aldehydes and Ketones by Vapor-Phase Hydrogen Transfer Reaction, Ballard et al., Shell Development Co., Emeryville, Calif., pp. 754-763, Mar. 16, 1956.

*Primary Examiner*—J. E. Evans
*Attorney, Agent, or Firm*—Sherman and Shalloway

[57] ABSTRACT

A catalyst for vapor-phase hydrogen transfer reaction between a carbonyl compound having an alkenyl or aryl group and a primary or secondary alcohol, said catalyst having a composition represented by the following general formula $$Mg_aX_bY_cO_d$$

wherein X represents at least one element selected from the group consisting of boron, aluminum, silicon, phosphorus, titanium, vanadium, iron, yttrium, zirconium, niobium, tin, antimony, lead, bismuth, lanthanum and cerium, Y represents at least one element selected from the group consisting of alkali metals and alkaline earth metals excepting magnesium, O represents oxygen, and a, b, c and d represent the atomic ratios of the individual elements, and when a is 1, b represents a number of 0.01 to 0.5, c represents a number of 0 to 0.5, and d is a number determined by the atomic valences and atomic ratios of the individual elements.

8 Claims, No Drawings

VAPOR-PHASE HYDROGEN TRANSFER REACTION OF CARBONYL COMPOUND WITH ALCOHOL

This application is a division of application Ser. No. 802,183, filed Nov. 25, 1985, now abandoned.

This invention relates to a catalyst for use in a vapor-phase hydrogen transfer reaction between a carbonyl compound having an alkenyl or aryl group and a primary or secondary alcohol, for example, schematically shown below.

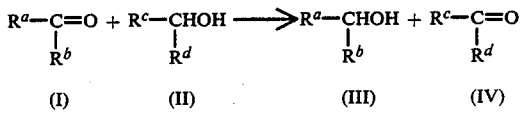

wherein $R^a$ and $R^b$ both represent a substituent having an alkenyl or aryl group, or one of them is a substituent having an alkenyl or aryl group and the other is hydrogen, and each of $R^c$ and $R^d$ represents hydrogen, an alkyl, hydroxyalkyl, alkenyl, phenyl or substituted phenyl group.

Alcohols of formula (III) that can be produced by this reaction have a wide range of applications, and are useful, for example, as important raw materials or intermediates in the fields of perfumes, medicines and polymers.

With regard to the production of alcohols (III) by selective hydrogenation of the carbonyl groups of carbonyl compounds of formula (I), the Nagase et al. method comprising hydrogenating the carbonyl compound in ethanol using a catalyst prepared by adding a trivalent iron compound to a Raney-type catalyst composed of silver and zinc [Chem. Lett., 1615, (1983)], and a method comprising hydrogenating the carbonyl compound in the presence of a rhodium catalyst and an amine [Bull. Chem. Soc., Jap., 50 (8), 2148, (1977)], for example, have been known heretofore. These methods are carried out under an elevated pressure of 50 to 80 kg/cm²-G, and moreover, the resulting alcohols should be separated from the solvent or the amine after the reaction. Hence, these methods require many process steps and much labor, and raise many problems in economy and productivity from the viewpoint of industrial production.

On the other hand, a method of selectively hydrogenating the carbonyl group of such a carbonyl compound as that of formula (I) by vapor-phase hydrogenation reaction would be very advantageous in regard to productivity. Such a method is described in the prior literature. For example, German Pat. No. 1,230,012 describes a method in which crotonaldehyde is converted to crotyl alcohol at a temperature of 200° C. and a pressure of 15 atmospheres by using a catalyst comprising cadmium, copper and magnesium. U.S. Pat. Nos. 4,072,727 and 4,096,193 describe a method in which acrolein is converted to allyl alcohol at a temperature of 100° to 200° C. and a pressure of 250 psi to 2,500 psi using a catalyst comprising silver and cadmium. These methods, however, require relatively high pressures. Furthermore, because the olefin bond portion of the starting carbonyl compound is hydrogenated at a high ratio, the selectivity of the desired alcohol is insufficient, and the method is far from being satisfactory.

One known method for hydrogen transfer reaction between an aldehyde and an alcohol as in the present invention is disclosed, for example, in U.S. Pat. No. 2,767,221. According to this method, acrolein is reacted with ethanol using a catalyst comprising magnesium oxide and zinc oxide to produce allyl alcohol (in a yield of 71.7% based on the consumed acrolein) and acetaldehyde. In this method, however, the conversion of the unsaturated aldehyde is low, and the primary or secondary alcohol must be used in a large excess relative to the unsaturated aldehyde. In addition, a tendency to a decrease in yield is observed after this catalyst is used for ten and several hours. Because of these disadvantages, the method of the above U.S. patent does not prove to be satisfactory from a practical viewpoint.

Generally, the production of an alcohol by hydrogenating a carbonyl compound having an alkenyl or aryl group in the vapor phase has the following problems.

(1) Since the alkenyl group is more easily hydrogenated than the carbonyl group, a large amount of a saturated aldehyde or saturated alcohol forms as a by-product.

(2) When an aldehyde having an aryl group is used as the carbonyl compound, side reactions such as the hydrogenation of the aryl group or the hydrogenolysis of the starting aldehyde occur, and it is difficult to obtain the desired alcohol in a high yield.

(3) In particular, when an alpha,beta-unsaturated carbonyl compound is used as the starting material, the selective hydrogenation of the carbonyl group becomes more difficult because of conjugation between its olefin bond and the carbonyl group. To increase the selectivity for an alpha,beta-unsaturated alcohol, relatively mild reaction conditions are required. This inevitably leads to a low conversion. Furthermore, even under the mild reaction conditions, the amount of saturated aldehyde and saturated alcohol as by-products are still large, and the yield of the desired alcohol is low.

It is an object of this invention therefore to provide a catalyst which can be used, without the inconveniences of the prior art discussed above, in a reaction of selective catalytic hydrogenation of the carbonyl group of a carbonyl compound having an alkenyl or aryl group using a primary or secondary alcohol as a hydrogen source (vapor phase hydrogen transfer reaction).

The vapor-phase hydrogen transfer reaction is a reaction whereby the starting carbonyl compound is converted to an alcohol by hydrogenation and the starting alcohol is converted to an aldehyde or ketone by dehydrogenation, and has the dual advantage that useful aldehydes and ketones can be simultaneously produced by properly varying the type of the starting alcohol.

Examples of suitable carbonyl compounds having an alkenyl or aryl group are shown below without any intention of limiting the invention thereto. Examples of carbonyl compounds having an alkenyl group are unsaturated aliphatic aldehydes or ketones having 3 to 10 carbon atoms such as (a) acrolein, (b) methacrolein, (c) crotonaldehyde, (d) methyl vinyl ketone, (e) senecioaldehyde, (f) 3-buten-1-one, (g) ethyl vinyl ketone and (h) 5-hexen-2-one. They will respectively be converted to the corresponding alcohols, i.e. (a') allyl alcohol, (b') methallyl alcohol, (c') crotyl alcohol, (d') 3-buten-2-ol, (e') 3-methyl-2-buten-1-ol, (f') 3-buten-1-ol, (g') 1-penten-3-ol and (h') 5-hexen-2-ol.

Examples of suitable carbonyl compounds having an aryl group are aromatic aldehydes or ketones represented by the following formula

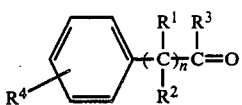  (I')

wherein each of $R^1$, $R^2$ and $R^3$ represents hydrogen or an alkyl group having 1 or 2 carbon atoms, $R^4$ represents hydrogen or an alkyl or alkoxy group having 1 to 4 carbon atoms, and n represents an integer in the range of 0 to 3. Specific examples of these are (i) benzaldehyde, (j) acetophenone, (k) phenylacetaldehyde, (l), m-tolualdehyde, (m), anisaldehyde and (n) cumic aldehyde. They will be converted respectively to (i') benzyl alcohol, (j') alpha-phenethyl alcohol, (k') beta-phenethyl alcohol, (l') 3-methylbenzyl alcohol, (m') anisyl alcohol, and (n') cumic alcohol.

Suitable examples of carbonyl compounds having both an alkenyl and an aryl group are aromatic aldehydes or ketones represented by the following formula

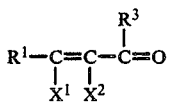  (I'')

wherein each of $X^1$ and $X^2$ represents hydrogen or

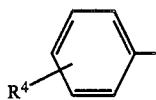

provided that they are not hydrogens at the same time, and $R^1$, $R^3$ and $R^4$ are as defined hereinabove. Specific examples of these are (o) cinnamic aldehyde and (p) atropaldehyde which will be converted respectively to (o') cinnamic alcohol and (p') 2-phenyl-2-propen-1-ol.

As primary or secondary alcohols used as a source of hydrogen suitable are alcohols having 1 to 9 carbon atoms represented by the formula

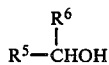  (II')

wherein each of $R^5$ and $R^6$ are selected from hydrogen, $C_1$-$C_8$ alkyl groups, $C_1$-$C_8$ hydroxyalkyl groups, $C_1$-$C_8$ alkenyl groups, a phenyl group and a benzyl group, provided that the sum of the number of carbons of $R^5$ and the number of carbons of $R^6$ is 0 to 8. Specific examples are monoalcohols such as methanol, ethanol, propanol, isopropanol, benzyl alcohol and phenethyl alcohol, and glycols such as ethylene glycol and 1,4-butanediol.

According to this invention, there is provided a catalyst capable of producing the desired alcohol in a high yield stably over an extended period of time in such a vapor phase hydrogen transfer reaction while the aforesaid problems of the prior art have been fully solved. This catalyst is represented by the general formula $Mg_aX_bY_cO_d$ wherein X represents at least one element selected from the group consisting of boron, aluminum, silicon, phosphorus, titanium, vanadium, iron, yttrium, zirconium, niobium, tin, antimony, lead, bismuth, lanthanum and cerium, Y represents at least one element selected from alkali metals and alkaline earth metals excepting magnesium, O represents oxygen, and a, b, c and d represent atomic ratios of the individual elements, and when a is 1, b represents a number of 0.01 to 0.5, c represents a number of 0 to 0.5, and d is represents a number determined by the atomic valences and atomic ratios of the individual elements.

The catalyst of this invention is prepared from various raw materials such as the oxides, hydroxides, halides, sulfates, nitrates and oxide sols of magnesium and the individual elements added (components X and Y). The use of the oxides or hydroxides is convenient in order to simplify the catalyst preparation method and minimize the evolution of gases during calcination.

For example, the catalyst of this invention may be prepared by a method which comprises dissolving or suspending the raw materials in water, and heating and concentrating the solution or suspension with stirring, followed by drying, molding and calcining; a method which comprises dissolving or suspending the raw materials in water, adding aqueous ammonia to form a hydroxide, followed by filtration, washing with water, drying, molding and calcining; or a method which comprises mixing the oxides or hydroxides of the individual elements in powder form, adding a suitable molding aid (such as water or alcohols), molding the mixture and drying and calcining the mixture.

The catalyst of this invention may be used as supported on a known inert carrier [preferably silica, alumina, Celite (trade name), etc.].

The temperature for catalyst calcination varies depending upon the type of the raw material, and can be in a wide range of 300° to 800° C., preferably 400° to 700° C.

The catalyst of this invention exhibits high activity when used in catalytic vapor-phase hydrogen transfer reaction between a carbonyl compound having an alkenyl or aryl group and a primary or secondary alcohol, and the selectivity of the desired alcohol is very high.

Even when this reaction is carried out for an extended period of time continuously, no deterioration in activity of the catalyst is observed, and the activity of the catalyst and the yield of the desired product are stable. Accordingly, the catalyst of this invention offers a full solution to the problem of the early deteriorating phenomenon which is considered to be most important in industrial production.

It has been noted that the catalyst of this invention exhibits much superior activity and selectivity to MgO or known hydrogen transfer reaction catalysts (such as MgO-ZnO). Presumably, this can be ascribed to the following mechanism. The addition of the component X in the present invention to magnesium element results in the addition of the active sites of the component X to the active sites (acid sites and base sites) of MgO and by the interaction of MgO with the component X, active sites having new properties appear. These active sites have an acidic nature and a basic nature suitable for the present reaction. In the acid sites the carbonyl group of the starting carbonyl compound is activated, and at the same time, the reaction of extracting hydrogen from the starting alcohol is activated at the base sites. Eventually, the activity of the catalyst to catalyze the desired hydrogen transfer reaction is increased.

The addition of the component Y which is an alkaline component is very effective for increasing the selectivity of the desired alcohol. This is presumably because the various acid sites formed by the addition of the component X are subtly controlled both qualitatively and quantitatively by the component Y so that they are suitable for the present reaction.

It is also noted that the performance of the catalyst of this invention is maintained over a surprisingly long period of time. Presumably, this is for the following reason. On the active sites of the catalyst of this invention as described above, the cycle of the catalytic reaction comprising the adsorption of the reactants and the desorption of the product is stably carried out. Furthermore, since the desorption of adsorbent materials such as water, carbon dioxide gas and carboxylic acids which are regarded as having a poisoning action on catalysts of this type takes place sufficiently rapidly, the phenomenon of deterioration in activity, which is generally regarded as being due to the extraordinarily strong adsorption of the absorbent materials does not occur.

In using the catalyst of this invention, the reactor may be a fixed bed flowing type or a fluidized bed type. The starting gas is prepared by mixing the starting carbonyl compound and primary or secondary alcohol in a mole ratio of from 1:0.5 to 1:20, preferably from 1:1 to 1:6, and if required, diluting the mixture with an inert gas such as nitrogen, helium or argon to a starting gas concentration of 1 to 80% by volume, preferably 2 to 50% by volume. The reaction is carried out usually under atmospheric pressure, but as required at elevated or reduced pressures. The reaction temperature is 150° to 400° C., preferably 200° to 350° C. The suitable space velocity of the starting gas varies depending upon the concentration of the starting gas, but is suitably 100 to 5,000 hr$^{-1}$, preferably 500 to 3,000 hr$^{-1}$.

The following examples illustrate the present invention more specifically.

In the examples, the conversion, selectivity and one-pass yield are defined as follows:

$$\text{Conversion (mole \%)} = \frac{\text{Moles of the consumed starting carbonyl compound}}{\text{Moles of the starting carbonyl compound fed}} \times 100$$

$$\text{Selectivity (mole \%)} = \frac{\text{Moles of the alcohol formed}}{\text{Moles of the consumed starting carbonyl compound}} \times 100$$

$$\text{One-pass yield (mole \%)} = \frac{\text{Moles of the alcohol formed}}{\text{Moles of the carbonyl compound fed}} \times 100$$

EXAMPLE 1

Magnesium hydroxide (25 g) and 0.6 g of boron oxide were suspended in 100 ml of water, and with sufficient stirring, the suspension was concentrated at 90° C. to give a white slurry-like mixture. The mixture was evaporated to dryness on a hot water bath, molded into a cylindrical form having an outside diameter of 5 mm and a height of 5 mm, and dried in an air atmosphere at 230° C. The dried product was calcined in an air atmosphere at 600° C. for 2 hours to prepare a catalyst.

Thirty milliliters of the catalyst was packed into a stainless steel U-shaped tube having an inside diameter of 20 mm, and a starting gas composed of acrolein, isopropyl alcohol and nitrogen in a volume ratio of 5:20:75 was passed through the tube at a space velocity of 1600 hr$^{-1}$ (STP) and continuously reacted. The reaction product was analyzed by gas chromatography, and the results shown in Table 1 were obtained.

EXAMPLE 2

Example 1 was repeated except that methacrolein and isopropanol were used as the raw materials. The results are shown in Table 1.

COMPARATIVE EXAMPLE 1

A catalyst was prepared in the same way as in Example 1 except that magnesium hydroxide alone was used as the raw material. By using this catalyst, the same reaction as in Example 1 was carried out. The results are shown in Table 1.

COMPARATIVE EXAMPLE 2

The same reaction as in Example 2 was carried out by using the catalyst prepared in Comparative Example 1.

EXAMPLE 3

Methacrolein and methanol were reacted by using the catalyst prepared in Example 1, and the results shown in Table 1 were obtained.

COMPARATIVE EXAMPLE 3

A catalyst having the composition $Mg_{1.0}Zn_{0.25}$ (atomic ratio excepting oxygen) was prepared in the same way as in Example 1 except that 8.77 g of zinc oxide was used instead of 0.6 g of boron oxide as a raw material for the component X. This catalyst had nearly the same composition as the catalyst disclosed in a working example in U.S. Pat. No. 2,767,221.

The same reaction as in Example 1 was carried out by using the resulting catalyst. The results are shown in Table 2.

COMPARATIVE EXAMPLE 4

The same reaction as in Example 2 was carried out except that the catalyst prepared in Comparative Example 3 was used. The results are shown in Table 2.

EXAMPLE 4

A catalyst having the composition $Mg_{1.0}Ce_{0.05}$ (atomic ratio excepting oxygen) was prepared in the same way as in Example 1 except that 3.71 g of cerium oxide was used instead of 0.6 g of boron oxide as a raw material for the component X. By using this catalyst, methacrolein and ethanol were reacted in the same way as in Example 1. The results are shown in Table 1.

EXAMPLE 5

A catalyst having the composition $Mg_{1.0}Si_{0.02}$ (atomic ratio excepting oxygen) was prepared in the same way as in Example 1 except that 0.52 g of silicon oxide was used instead of 0.6 g of boron oxide as a raw material for the component X. By using this catalyst, methacrolein and benzyl alcohol were reacted in the same way as in Example 1. The results are shown in Table 1.

EXAMPLE 6

A catalyst having the composition $Mg_{1.0}Bi_{0.04}$ (atomic ratio excepting oxygen) was prepared in the same way as in Example 1 except that 0.48 g of bismuth hydroxide was used instead of 0.6 g of boron oxide as a raw material for the component X. By using this catalyst, crotonaldehyde and n-butanol were reacted in the same way as in Example 1. The results are shown in Table 1.

EXAMPLE 7

A catalyst having the composition $Mg_{1.0}Zr_{0.03}$ (atomic ratio excepting oxygen) was prepared in the same way as in Example 1 except that 1.59 g of zirconium oxide was used instead of 0.6 g of boron oxide as a raw material for the component X. By using this catalyst, methyl vinyl ketone and 1,4-butanediol were reacted in the same way as in Example 1. The results are shown in Table 1.

EXAMPLE 8

A catalyst having the composition $Mg_{1.0}La_{0.05}$ (excepting oxygen) was prepared in the same way as in Example 1 except that 3.51 g of lanthanum oxide was used instead of 0.6 g of boron oxide as a raw material for the component X. By using this catalyst, ethyl vinyl ketone and 3-methyl-1-butanol were reacted in the same way as in Example 1. The results are shown in Table 1.

EXAMPLE 9

A catalyst having the composition $Mg_{1.0}Ti_{0.05}$ (atomic ratio excepting oxygen) was prepared in the same way as in Example 1 except that 1.72 g of titanium dioxide was used instead of 0.6 g of boron oxide as a raw material for the component X. By using this catalyst, 5-hexen-2-one and phenethyl alcohol were reacted in the same way as in Example 1. The results are shown in Table 1.

EXAMPLE 10

A catalyst having the composition $Mg_{1.0}B_{0.01}Ce_{0.05}$ (atomic ratio excepting oxygen) was prepared in the same way as in Example 1 except that 0.15 g of boron oxide and 3.71 g of cerium oxide were used as raw materials for the component X. By using this catalyst, 2-cyclohexen-1-one and cyclohexanol were reacted in the same way as in Example 1. The results are shown in Table 1.

EXAMPLE 11

A catalyst having the composition $Mg_{1.0}P_{0.01}Ti_{0.1}$ (atomic ratio excepting oxygen) was prepared in the same way as in Example 1 except that 0.50 g of phosphoric acid (85%) and 3.45 g of titanium oxide were used as raw materials for the component X. By using this catalyst, senecioaldehyde and 2-butanol were reacted in the same way as in Example 1. The results are shown in Table 1.

EXAMPLE 12

A catalyst having the composition $Mg_{1.0}Al_{0.01}Zr_{0.02}$ (atomic ratio excepting oxygen) was prepared in the same way as in Example 1 except that 0.22 g of aluminum oxide and 1.06 g of zirconium oxide were used as raw materials for the component X. By using this catalyst, 3-buten-1-one and n-hexanol were reacted in the same way as in Example 1. The results are shown in Table 1.

EXAMPLE 13

A catalyst having the composition $Mg_{1.0}Si_{0.05}Pb_{0.01}$ (atomic ratio excepting oxygen) was prepared in the same way as in Example 1 except that 1.29 g of silicon dioxide and 1.43 g of lead nitrate were used as raw materials for the component X. By using this catalyst, methacrolein and n-propanol was reacted in the same way as in Example 1. The results are shown in Table 1.

EXAMPLE 14

A catalyst having the composition $Mg_{1.0}B_{0.03}Nb_{0.02}$ (atomic ratio excepting oxygen) was prepared in the same way as in Example 1 except that 0.45 g of boron oxide and 1.15 g of niobium pentoxide were used as raw materials for the component X. By using this catalyst, the same reaction as in Example 2 was carried out. The results are shown in Table 1.

EXAMPLE 15

Magnesium hydroxide (25 g) and 2.59 g of silicon dioxide as a source of the component X were suspended in 100 ml of water, and with thorough stirring, the suspension was heated to 90° C. Then, a solution of 0.24 g of potassium hydroxide as a source of the component Y in 10 ml of water was added, and the mixture was concentrated under heat to give a white slurry-like mixture. The mixture was evaporated to dryness over a hot water bath, molded into a cylindrical form having an outside diameter of 5 mm and a height of 5 mm, and calcined in an air atmosphere at 600° C. for 2 hours to give a catalyst having the composition $Mg_{1.0}Si_{0.1}K_{0.01}$ (atomic ratio excepting oxygen).

By using this catalyst, methacrolein and isopropanol were reacted in the same way as in Example 1 except that the mole ratio of methacrolein to isopropanol was adjusted to 3 and the reaction temperature was varied as indicated in Table 1. The results are shown in Table 1.

EXAMPLE 16

A catalyst having the composition $Mg_{1.0}Al_{0.01}V_{0.01}Cs_{0.01}$ (atomic ratio excepting oxygen) was prepared in the same way as in Example 15 except that 0.22 g of aluminum oxide and 0.39 g of vanadium pentoxide were used as raw materials for the component X and 0.65 g of cesium hydroxide was used as a raw material for the component Y. By using this catalyst, the same reaction as in Example 15 was carried out. The results are shown in Table 1.

EXAMPLE 17

A catalyst having the composition $Mg_{1.0}P_{0.02}Y_{0.01}Li_{0.01}$ (atomic ratio excepting oxygen) was prepared in the same way as in Example 15 except that 0.99 g of 85% phosphoric acid and 0.49 g of yttrium oxide were used as raw materials for the component X and 0.10 g of lithium hydroxide was used as a raw material for the component Y. By using this catalyst, the same reaction as in Example 15 was carried out. The results are shown in Table 1.

EXAMPLE 18

A catalyst having the composition $Mg_{1.0}Si_{0.08}Sb_{0.04}Ba_{0.01}Rb_{0.01}$ (atomic ratio excepting oxygen) was prepared in the same way as in Example 15 except that 2.07 g of silicon dioxide and 2.51 g of antimony trioxide were used as raw materials for the component X, and 0.74 g of barium hydroxide and 0.44 g of rubidium hydroxide were used asd raw materials for the component Y. By using this catalyst, acrolein and isopropanol were reacted in the same way as in Example 15. The results are shown in Table 1.

EXAMPLE 19

A catalyst having the composition $Mg_{1.0}B_{0.02}Si_{0.1}Ca_{0.01}Na_{0.01}$ (atomic ratio excepting oxygen) was prepared in the same way as in Example 15 except that 0.30 g of boron oxide and 2.59 g of silicon dioxide were used as raw materials for the component X, and 0.32 g of calcium hydroxide and 0.17 g of sodium hydroxide were used as raw materials for the component Y. By using this catalyst, crotonaldehyde and isopropanol were reacted in the same way as in Example 15. The results are shown in Table 1.

EXAMPLE 20

A catalyst having the composition $Mg_{1.0}Si_{0.05}Sn_{0.05}Na_{0.01}$ (atomic ratio excepting oxygen) was prepared in the same way as in Example 15 except that 1.29 g of silicon dioxide and 2.90 g of stannous oxide were used as raw materials for the component X, and 0.17 g of sodium hydroxide were used as a raw material for the component Y. By using this catalyst, 5-hexen-2-one and isopropanol were reacted in the same way as in Example 15. The results are shown in Table 1.

EXAMPLE 21

A catalyst having the composition $Mg_{1.0}Si_{0.2}Ti_{0.1}Sr_{0.03}K_{0.02}$ (atomic ratio excepting oxygen) was prepared in the same way as in Example 15 except that 5.17 g of silicon dioxide and 3.44 g of titanium dioxide were used as raw materials for the component X, and 1.57 g of strontium hydroxide and 0.48 g of potassium hydroxide were used as raw materials for the component Y. By using this catalyst, methyl vinyl ketone and isopropanol were reacted in the same way as in Example 15. The results are shown in Table 1.

EXAMPLE 22

A catalyst having the composition $Mg_{1.0}Si_{0.1}Fe_{0.05}La_{0.02}K_{0.01}$ (atomic ratio excepting oxygen) was prepared in the same way as in Example 15 except that 2.59 g of silicon dioxide, 1.72 g of ferric oxide and 1.40 g of lanthanum oxide were used as raw materials for the component X, and 0.24 g of potassium hydroxide were used asd raw materials for the component Y. By using this catalyst, methacrolein and isopropanol were reacted in the same way as in Example 15. The results are shown in Table 1.

TABLE 1-a

| Example | Mg | Component X | | Component Y | | Carbonyl compound | Alcohol | Mole ratio of the alcohol to carbonyl compound |
|---|---|---|---|---|---|---|---|---|
| 1 | 1 | B | 0.04 | — | | acrolein | isopropanol | 4 |
| 2 | 1 | B | 0.04 | — | | methacrolein | isopropanol | 4 |
| 3 | 1 | B | 0.04 | — | | methacrolein | methanol | 4 |
| 4 | 1 | Ce | 0.05 | — | | methacrolein | ethanol | 4 |
| 5 | 1 | Si | 0.02 | — | | methacrolein | benzyl alcohol | 4 |
| 6 | 1 | Bi | 0.04 | — | | crotonaldehyde | n-butanol | 4 |
| 7 | 1 | Zr | 0.03 | — | | methyl vinyl ketone | 1,4-butanediol | 4 |
| 8 | 1 | La | 0.05 | — | | ethyl vinyl ketone | 3-methyl-1-butanol | 4 |
| 9 | 1 | Ti | 0.05 | — | | 5-hexen-2-one | beta-phenethyl alcohol | 4 |
| 10 | 1 | B<br>Ce | 0.01<br>0.05 | — | | 2-cyclohexene-1-one | cyclohexanol | 4 |
| 11 | 1 | P<br>Ti | 0.01<br>0.1 | — | | senecioaldehyde | 2-butanol | 4 |
| 12 | 1 | Al<br>Zr | 0.01<br>0.02 | — | | 3-buten-1-one | n-hexanol | 4 |
| 13 | 1 | Si<br>Pb | 0.05<br>0.01 | — | | methacrolein | n-propanol | 4 |
| 14 | 1 | B<br>Nb | 0.03<br>0.02 | — | | methacrolein | isopropanol | 4 |
| 15 | 1 | Si | 0.1 | K | 0.01 | methacrolein | isopropanol | 3 |
| 16 | 1 | Al<br>V | 0.01<br>0.01 | Cs | 0.01 | methacrolein | isopropanol | 3 |
| 17 | 1 | P<br>Y | 0.02<br>0.01 | Li | 0.01 | methacrolein | isopropanol | 3 |
| 18 | 1 | Si<br>Sb | 0.08<br>0.04 | Ba<br>Rb | 0.01<br>0.01 | acrolein | isopropanol | 3 |
| 19 | 1 | B<br>Si | 0.02<br>0.1 | Ca<br>Na | 0.01<br>0.01 | crotonaldehyde | isopropanol | 3 |
| 20 | 1 | Si<br>Sn | 0.05<br>0.05 | Na | 0.01 | 5-hexen-2-one | isopropanol | 3 |
| 21 | 1 | Si<br>Ti | 0.2<br>0.1 | Sr<br>K | 0.03<br>0.02 | methyl vinyl ketone | isopropanol | 3 |
| 22 | 1 | Si<br>Fe<br>La | 0.1<br>0.05<br>0.02 | K | 0.01 | methacrolein | isopropanol | 3 |

TABLE 1-b

| Example | Reaction temperature (°C.) | Reaction time elapsed (hrs) | Conversion of the carbonyl compound (mole %) | Alcohol formed | Selectivity of the alcohol (based on carbonyl compound, mole %) | One-pass yield of the alcohol (based on carbonyl compound, mole %) |
|---|---|---|---|---|---|---|
| 1 | 270 | 2 | 89.6 | allyl alcohol | 92.3 | 82.7 |
|  |  | 150 | 89.4 |  | 92.6 | 82.8 |
| 2 | 270 | 2 | 90.2 | methallyl alcohol | 94.5 | 85.2 |
|  |  | 150 | 90.8 |  | 95.5 | 86.7 |
| 3 | 300 | 2 | 62.3 | methallyl alcohol | 89.6 | 55.8 |
| 4 | 270 | 2 | 73.3 | methallyl alcohol | 92.1 | 67.5 |
|  |  | 150 | 72.1 |  | 93.0 | 67.1 |
| 5 | 270 | 2 | 85.6 | methallyl alcohol | 96.5 | 82.6 |
| 6 | 260 | 2 | 96.6 | crotonyl alcohol | 93.2 | 90.0 |
| 7 | 250 | 2 | 100 | 3-buten-2-ol | 96.2 | 96.2 |
| 8 | 260 | 2 | 100 | 1-penten-3-ol | 95.0 | 95.0 |
| 9 | 260 | 2 | 97.2 | 5-hexen-2-ol | 100 | 97.2 |
| 10 | 270 | 2 | 84.8 | 2-cyclohexan-1-ol | 90.6 | 76.8 |
| 11 | 270 | 2 | 88.3 | 3-methyl-2-buten-1-ol | 93.1 | 82.2 |
| 12 | 280 | 2 | 93.3 | 3-buten-1-ol | 98.9 | 92.3 |
| 13 | 270 | 2 | 83.4 | methallyl alcohol | 93.1 | 77.6 |
| 14 | 260 | 2 | 94.1 | methallyl alcohol | 97.2 | 91.5 |
| 15 | 260 | 2 | 96.6 | methallyl alcohol | 97.8 | 94.5 |
|  |  | 150 | 95.7 |  | 98.3 | 94.1 |
| 16 | 250 | 2 | 96.9 | methallyl alcohol | 88.0 | 85.3 |
| 17 | 270 | 2 | 96.1 | methallyl alcohol | 93.8 | 90.1 |
| 18 | 200 | 2 | 93.8 | allyl alcohol | 96.4 | 90.4 |
| 19 | 200 | 2 | 95.3 | crotonyl alcohol | 89.4 | 85.2 |
| 20 | 230 | 2 | 98.6 | 5-hexen-2-ol | 100 | 98.6 |
| 21 | 200 | 2 | 99.3 | 3-butene-2-al | 98.3 | 97.6 |
| 22 | 270 | 2 | 97.8 | methallyl alcohol | 98.2 | 96.0 |

TABLE 2-a

| Comparative Example | Catalyst composition (atomic ratio excepting oxygen) | | | Starting materials | | Mole ratio of the alcohol to carbonyl compound |
|---|---|---|---|---|---|---|
|  | Mg | Component X | Component Y | Carbonyl compound | Alcohol |  |
| 1 | 1 | — | — | acrolein | isopropanol | 4 |
| 2 | 1 | — | — | methacrolein | isopropanol | 4 |
| 3 | 1 | Zn 0.25 | — | acrolein | isopropanol | 4 |
| 4 | 1 | Zn 0.25 | — | methacrolein | isopropanol | 4 |

TABLE 2-b

| Comparative Example | Reaction temperature (°C.) | Reaction time elapsed (hrs) | Conversion of the carbonyl compound (mole %) | Alcohol formed | Selectivity of the alcohol (based on carbonyl compound, mole %) | One-pass yield of the alcohol (based on carbonyl compound, mole %) |
|---|---|---|---|---|---|---|
| 1 | 270 | 2 | 57.0 | allyl alcohol | 90.5 | 51.6 |
|  |  | 20 | 41.8 |  | 91.6 | 38.3 |
| 2 | 270 | 2 | 60.2 | methallyl alcohol | 91.2 | 54.9 |
|  |  | 20 | 43.3 |  | 92.0 | 39.8 |
| 3 | 270 | 2 | 55.4 | allyl alcohol | 85.3 | 47.3 |
| 4 | 270 | 2 | 59.5 | methallyl alcohol | 87.7 | 52.2 |
|  |  | 50 | 45.1 |  | 88.6 | 40.0 |

EXAMPLE 23

Magnesium hydroxide (500 g) and 59.7 g of boron oxide were suspended in 1500 ml of water, and with stirring, the mixture was heated to 90° C. to concentrate it. The resulting white slurry was dried at 120° C. and then pulverized. Water was added to the pulverized product as a molding aid, and the mixture was extruded into a cylindrical shape having a diameter of 5 mm and a length of 5 mm. The molded product was dried at 230° C., and calcined at 600° C. for 2 hours in an air atmosphere to give a catalyst having the composition $Mg_{1.0}B_{0.2}$ (atomic ratio excepting oxygen).

Thirty milliliters of this catalyst was packed into the same reaction tube as used in Example 1, and a methacrolein and isopropanol were continuously reacted in it. As a source of methacrolein used as a material in this reaction, there was used a reaction product gas containing methacrolein which obtained in the production of methacrolein by the catalytic vapor-phase oxidation of t-butanol. The product gas had the average composition shown in Table 3.

TABLE 3

| Component | Volume % |
|---|---|
| methacrolein | 4.3 |
| Water | 9.7 |
| Methacrylic acid and acetic acid | 0.24 |
| Acrolein, acetone and acetaldehyde | 0.08 |
| iso-Butylene | 0.3 |
| Carbon dioxide | 0.23 |
| Carbon monoxide | 0.04 |
| Oxygen | 2.4 |
| Nitrogen | 82.7 |

The reaction temperature was maintained at 290° C. and the mole ratio of isopropanol to methacrolein, at 3. Nitrogen was further supplied so that the space velocity became 1600 hr$^{-1}$. Under these conditions, the reaction was carried out continuously for 2,000 hours. The results are shown in Table 4.

TABLE 4

| Reaction time elapsed (hours) | Conversion of methacrolein (mole % based on methacrolein) | Selectivity of methallyl alcohol (mole % based on methacrolein) | One-pass yield of methallyl alcohol (mole % based on methacrolein) |
|---|---|---|---|
| 2 | 84.1 | 91.7 | 77.1 |
| 1000 | 83.6 | 91.8 | 76.7 |
| 2000 | 83.9 | 91.3 | 76.6 |

EXAMPLE 24

The same continuous reaction as in Example 23 was carried out by using the catalyst prepared in Example 22. The results are shown in Table 5.

TABLE 5

| Reaction time elapsed (hours) | Conversion of methacrolein (mole % based on methacrolein) | Selectivity of methallyl alcohol (mole % based on methacrolein) | One-pass yield of methallyl alcohol (mole % based on methacrolein) |
|---|---|---|---|
| 2 | 93.5 | 97.2 | 90.9 |
| 1000 | 93.1 | 97.0 | 90.3 |
| 2000 | 92.0 | 96.8 | 89.1 |

EXAMPLE 25

The same reaction as in Example 1 was carried out except that benzaldehyde and methanol were used as the starting materials, and the reaction temperature was changed to 290° C. The results are shown in Table 6.

EXAMPLE 26

The same reaction as in Example 1 was carried out except that benzaldehyde and ethanol were used as the starting materials. The results are shown in Table 6.

COMPARATIVE EXAMPLE 5

A catalyst was prepared in the same way as in Example 1 except that magnesium hydroxide alone was used as the raw material. By using this catalyst, the same reaction as in Example 26 was carried out. In the early stage of the reaction, an aldehyde conversion of 52.9% was obtained. On continuing the reaction, the catalyst lost its activity in about 20 hours.

EXAMPLE 27

By using the catalyst prepared in Example 7, acetophenone and n-propanol were reacted in the same way as in Example 1. The results are shown in Table 6.

EXAMPLE 28

By using the catalyst prepared in Example 11, acetophenone and isopropanol were reacted in the same way as in Example 1. The results are shown in Table 6.

EXAMPLE 29

A catalyst having the composition $Mg_{1.0}B_{0.02}Zr_{0.02}$ (atomic ratio excepting oxygen) was prepared in the same way as in Example 1 except that 0.30 g of boron oxide and 1.06 g of zirconium oxide were used as raw materials for the component X. By using this catalyst, cumic aldehyde and 2-butanol were reacted in the same way as in Example 1. The results are shown in Table 6.

EXAMPLE 30

A catalyst having the composition $Mg_{1.0}Ce_{0.05}V_{0.01}Pb_{0.01}$ (atomic ratio excepting oxygen) was prepared in the same way as in Example 1 except that 3.71 g of cerium oxide, 0.39 g of vanadium pentoxide and 1.43 g of lead nitrate were used as raw materials for the component X. By using this catalyst, m-tolualdehyde and isopropanol were reacted in the same way as in Example 1. The results are shown in Table 6.

COMPARATIVE EXAMPLE 6

The same reaction as in Example 30 was carried out by using the same catalyst (MgO) as in Comparative Example 5. As shown in Table 7, an aldehyde conversion of 62.4% was obtained in the early stage of the reaction. On continuing the reaction, however, the catalyst lost its activity in about 20 hours.

EXAMPLE 31

A catalyst having the composition $Mg_{1.0}Si_{0.02}K_{0.01}$ (atomic ratio excepting oxygen) was prepared in the same way as in Example 15 except that 0.52 g of silicon dioxide was used as a material for the component X and 0.24 g of potassium hydroxide was used as a material for the component Y. By using this catalyst, m-tolualdehyde and 1,4-butanediol were reacted in the same way as in Example 11. The results are shown in Table 6.

EXAMPLE 32

A catalyst having the composition $Mg_{1.0}Si_{0.1}Nb_{0.01}K_{0.01}$ (atomic ratio excepting oxygen) was prepared in the same way as in Example 15 except that 2.59 g of silicon dioxide and 0.57 g of niobium pentoxide were used as materials for the component X, and 0.24 g of potassium hydroxide was used as a material for the component Y. By using this catalyst, anisaldehyde and isopropanol were reacted in the same way as in Example 15 except that the mole ratio of anisaldehyde to isopropanol was maintained at 1:3. The results are shown in Table 6.

EXAMPLE 33

A catalyst having the composition $Mg_{1.0}Bi_{0.05}Al_{0.05}Na_{0.01}Ca_{0.03}$ (atomic ratio excepting oxygen) was prepared in the same way as in Example 15 except that 5.60 g of bismuth hydroxide and 1.10 g of aluminum oxide were used as materials for the component X, and 0.17 g of sodium hydroxide and 0.96 g of calcium hydroxide were used as materials for the component Y. By using this catalyst, anisaldehyde and benzyl alcohol were reacted in the same way as in Example 15. The results are shown in Table 6.

EXAMPLE 34

A catalyst having the composition $Mg_{1.0}Si_{0.2}Sn_{0.05}Ti_{0.05}Li_{0.02}Sr_{0.03}$ (atomic ratio excepting oxygen) was prepared in the same way as in Example 15 except that 5.17 g of silicon dioxide, 2.90 g of stannous oxide and 1.72 g of titanium dioxide were used as materials for the component X, and 0.21 g of lithium hydroxide and 1.57 g of strontium hydroxide were used as materials for the component Y. By using this catalyst, anisaldehyde and beta-phenethyl alcohol were reacted in the same way as in Example 15. The results are shown in Table 6.

EXAMPLE 35

A catalyst having the composition $Mg_{1.0}B_{0.02}Ti_{0.05}Na_{0.01}Ba_{0.03}$ (atomic ratio excepting oxygen) was prepared in the same way as in Example 15 except that 0.30 g of boron oxide and 1.72 g of titanium oxide were used as materials for the component X, and 0.17 g of sodium hydroxide and 2.22 g of barium hydroxide were used as materials for the component Y. By using this catalyst, phenylacetaldehyde and cyclohexanol were reacted in the same way as in Example 15. The results are shown in Table 6.

EXAMPLE 36

A catalyst having the composition $Mg_{1.0}Si_{0.1}Sb_{0.05}La_{0.02}K_{0.01}$ (atomic ratio excepting oxygen) was prepared in the same way as in Example 15 except that 2.59 g of silicon dioxide, 3.14 g of antimony trioxide and 1.40 g of lanthanum oxide were used as materials for the component X, and 0.24 g of potassium hydroxide was used as a material for the component Y. By using this catalyst, cinnamic aldehyde and isopropanol were reacted in the same way as in Example 15. The results are shown in Table 6.

EXAMPLE 37

A catalyst having the composition $Mg_{1.0}Si_{0.1}Fe_{0.05}Y_{0.02}K_{0.01}Ba_{0.04}$ (atomic ratio excepting oxygen) was prepared in the same way as in Example 15 except that 2.59 g of silicon dioxide, 1.72 g of ferric oxide and 0.97 g of yttrium oxide were used as materials for the component X, and 0.24 g of poassium hydroxide and 2.95 g of barium hydroxide were used as materials for the component Y. By using this catalyst, atropaldehyde and isopropanol were reacted in the same way as in Example 15. The results are shown in Table 6.

COMPARATIVE EXAMPLE 7

The same reaction as in Example 32 was carried out except that a catalyst composed of magnesium oxide and zinc oxide (in a mole ratio of 4:1) was used, and the mole ratio of the alcohol to aldehyde was maintained at 4:1.

The catalyst used in this example had the same composition as that disclosed in U.S. Pat. No. 2,767,221 as a catalyst for synthesis of unsaturated alcohols.

TABLE 6-a

| Example | Mg | Catalyst composition (atomic ratio excepting oxygen) Component X | | Component Y | | Starting materials Carbonyl compound | Alcohol | Mole ratio of the alcohol to carbonyl compound |
|---|---|---|---|---|---|---|---|---|
| 25 | 1 | B | 0.04 | — | | benzaldehyde | methanol | 4 |
| 26 | 1 | B | 0.04 | — | | benzaldehyde | ethanol | 4 |
| 27 | 1 | Zr | 0.03 | — | | acetophenone | n-propanol | 4 |
| 28 | 1 | P | 0.01 | — | | acetophenone | isopropanol | 4 |
|   |   | Ti | 0.1 |   |   |   |   |   |
| 29 | 1 | B | 0.02 | — | | cumic aldehyde | 2-butanol | 4 |
|   |   | Zr | 0.02 |   |   |   |   |   |
| 30 | 1 | Ce | 0.05 | — | | m-tolualdehyde | isopropanol | 4 |
|   |   | V | 0.01 |   |   |   |   |   |
|   |   | Pb | 0.01 |   |   |   |   |   |
| 31 | 1 | Si | 0.02 | K | 0.01 | m-tolualdehyde | 1,4-butanediol | 4 |
| 32 | 1 | Si | 0.1 | K | 0.01 | anisaldehyde | isopropanol | 3 |
|   |   | Nb | 0.01 |   |   |   |   |   |
| 33 | 1 | Bi | 0.05 | Na | 0.01 | anisaldehyde | benzyl alcohol | 3 |
|   |   | Al | 0.05 | Ca | 0.03 |   |   |   |
| 34 | 1 | Si | 0.2 | Li | 0.02 | anisaldehyde | beta-phenethyl alcohol | 3 |
|   |   | Sn | 0.05 | Sr | 0.03 |   |   |   |
|   |   | Ti | 0.05 |   |   |   |   |   |
| 35 | 1 | B | 0.02 | Na | 0.01 | phenylacet-aldehyde | cyclohexanol | 3 |
|   |   | Ti | 0.05 | Ba | 0.03 |   |   |   |
| 36 | 1 | Si | 0.1 | K | 0.1 | cinnamic aldehyde | isopropanol | 3 |
|   |   | Sb | 0.05 |   |   |   |   |   |
|   |   | La | 0.02 |   |   |   |   |   |
| 37 | 1 | Si | 0.1 | K | 0.01 | atropaldehyde | isopropanol | 3 |
|   |   | Fe | 0.05 | Ba | 0.04 |   |   |   |
|   |   | Y | 0.02 |   |   |   |   |   |

TABLE 6-b

| Example | Reaction temperature (°C.) | Reaction time elapsed (hrs) | Conversion of the carbonyl compound (mole %) | Alcohol formed | Selectivity of the alcohol (based on carbonyl compound, mole %) | One-pass yield of the alcohol (based on carbonyl compound, mole %) |
|---|---|---|---|---|---|---|
| 25 | 290 | 2 | 78.6 | benzyl alcohol | 95.8 | 75.3 |
| 26 | 270 | 2 | 85.6 | benzyl alcohol | 97.2 | 83.2 |
|   |   | 150 | 85.0 |   | 97.7 | 83.0 |
| 27 | 260 | 2 | 94.8 | alpha-phenethyl alcohol | 100 | 94.8 |
| 28 | 260 | 2 | 100 | alpha-phenethyl alcohol | 99.8 | 99.8 |
|   |   | 150 | 100 |   | 100 | 100 |
| 29 | 260 | 2 | 98.2 | cumic alcohol | 99.0 | 97.2 |
| 30 | 270 | 2 | 99.6 | 3-methyl benzyl alcohol | 100 | 99.6 |
|   |   | 150 | 99.4 |   | 100 | 99.4 |
| 31 | 260 | 2 | 99.5 | 3-methyl-benzyl alcohol | 100 | 99.5 |
| 32 | 270 | 2 | 100 | anisyl alcohol | 100 | 100 |

TABLE 6-b-continued

| Example | Reaction temperature (°C.) | Reaction time elapsed (hrs) | Conversion of the carbonyl compound (mole %) | Alcohol formed | Selectivity of the alcohol (based on carbonyl compound, mole %) | One-pass yield of the alcohol (based on carbonyl compound, mole %) |
|---|---|---|---|---|---|---|
|  |  | 200 | 99.8 |  | 100 | 99.8 |
| 33 | 270 | 2 | 100 | anisyl alcohol | 100 | 100 |
| 34 | 270 | 2 | 100 | anisyl alcohol | 100 | 100 |
| 35 | 270 | 2 | 99.1 | beta-phenethyl alcohol | 99.9 | 99.0 |
| 36 | 270 | 2 | 100 | cinnamyl alcohol | 97.2 | 97.2 |
| 37 | 270 | 2 | 100 | 2-phenyl-2-propen-1-ol | 95.1 | 95.1 |

TABLE 7-a

| Comparative Example | Catalyst composition (atomic ratio excepting oxygen) | | | Starting materials | | Mole ratio of the alcohol to carbonyl compound |
|---|---|---|---|---|---|---|
|  | Mg | Component X | Component Y | Carbonyl compound | Alcohol |  |
| 5 | 1 | — | — | benzaldehyde | ethanol | 4 |
| 6 | 1 | — | — | m-tolualdehyde | isopropanol | 4 |
| 7 | 1 | Zn 0.25 | — | anisaldehyde | isopropanol | 4 |

TABLE 7-b

| Comparative Example | Reaction temperature (°C.) | Reaction time elapsed (hrs) | Conversion of the carbonyl compound (mole %) | Alcohol formed | Selectivity of the alcohol (based on carbonyl compound, mole %) | One-pass yield of the alcohol (based on carbonyl compound, mole %) |
|---|---|---|---|---|---|---|
| 5 | 270 | 2 | 52.9 | benzyl alcohol | 100 | 52.9 |
| 6 | 270 | 2 | 62.4 | 2-methyl benzyl alcohol | 100 | 62.4 |
| 7 | 270 | 2 | 65.4 | anisyl alcohol | 100 | 65.4 |
|  |  | 20 | 33.2 |  | 100 | 33.2 |

What is claimed is:

1. In a vapor-phase hydrogen transfer reaction for reacting in the vapor-phase a carbonyl compound having an alkenyl or aryl group and a primary or secondary alcohol in the presence of a vapor-phase hydrogen transfer catalyst, the improvement comprising carrying out said reaction in the presence of a catalyst having a composition represented by the following formula $$Mg_aX_bY_cO_d$$

wherein X represents at least one element selected from the group consisting of boron, aluminum, silicon, phosphorus, titanium, vanadium, yttrium, zirconium, niobium, tin, antimony, lead, bismuth, lanthanum and cerium, Y represents at least one element selected from the group consisting of alkali metals and alkaline earth metals excepting magnesium, O represents oxygen, and a, b, c and d represent the atomic ratios of the individual elements, and when a is 1, b represents a number of 0.01 to 0.5, c represents a number of 0 to 0.5, and d is a number determined by the atomic valences and atomic ratios of the individual elements.

2. A vapor-phase hydrogen transfer reaction according to claim 1 for preparing an unsaturated aliphatic alcohol which comprises reacting an unsaturated aliphatic aldehyde or ketone having 3 to 10 carbon atoms and a primary or secondary alcohol having 1 to 9 carbon atoms in the vapor-phase in the presence of the catalyst composition of said formula.

3. The process of claim 2 wherein the unsaturated aliphatic aldehyde or ketone is selected from the group consisting of acrolein, methacrolein, crotonaldehyde, methyl vinyl ketone, senecioaldehyde, 3-buten-1-one, ethyl vinyl ketone and 5-hexen-2-one.

4. The process of claim 3 wherein the primary or secondary alcohol is selected from the group consisting methanol, ethanol, propanol, isopropanol, benzyl alcohol, phenethyl alcohol, ethylene glycol and 1,4-butane diol.

5. A vapor-phase hydrogen transfer reaction according to claim 1 for preparing an aromatic alcohol which comprises reacting an aromatic aldehyde or ketone represented by the general formula.

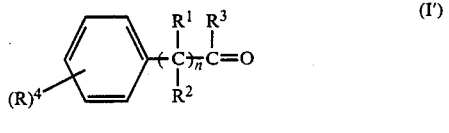

(I')

or

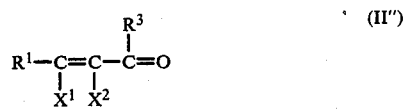

(II")

wherein each of $R^1$, $R^2$ and $R^3$ is selected from the class of hydrogen and alkyl groups having 1–2 carbon atoms, $R^4$ is selected from the class of hydrogen, alkyl groups having 1 to 4 carbon atoms and alkoxy groups having 1 to 4 carbon atoms, n represents an integer in the range of 0 to 3, and each of $X^1$ and $X^2$ is selected from the class of hydrogen and

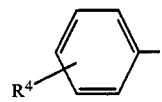

but $X^1$ and $X^2$ are not hydrogens at the same time, and a primary or secondary alcohol represented by the general formula

(II')

wherein each of $R^5$ and $R^6$ is selected from the class of hydrogen, alkyl groups having 1 to 8 carbon atoms, hydroxyalkyl groups having 1 to 8 carbon atoms, alkenyl groups having 1 to 8 carbon atoms, a phenyl group and a benzyl group, provided that the sum of the number of carbon atoms of $R^5$ and the number of carbon atoms of $R^6$ is 0 to 8, in the vapor-phase in the presence of the catalyst composition of said formula.

6. The process of claim 5 wherein the aromatic aldehyde or ketone is a compound of the formula (I') and is selected from the group consisting of benzaldehyde, acetophenone, phenylacetaldehyde, m-tolualdehyde, anisaldehyde and cumic aldehyde.

7. The process of claim 5 wherein the aromatic aldehyde or ketone is represented by the formula (I'') and is selected from the group consisting of cinnamic aldehyde and atropaldehyde.

8. The process of claim 1 wherein c represents a number of from 0.01 to 0.05.

* * * * *